US009028065B2

(12) United States Patent
Yokoi et al.

(10) Patent No.: US 9,028,065 B2
(45) Date of Patent: May 12, 2015

(54) OPHTHALMOLOGIC APPARATUS AND IMAGE CLASSIFICATION METHOD

(75) Inventors: Norihiko Yokoi, Kyoto (JP); Yutaka Mizukusa, Hamamatsu (JP); Shigeru Kinoshita, Osaka (JP)

(73) Assignees: Kowa Company, Ltd. (JP); Kyoto Prefetural Public University Corporation (JP)

( * ) Notice: Subject to any disclaimer, the term of this patent is extended or adjusted under 35 U.S.C. 154(b) by 0 days.

(21) Appl. No.: 13/575,635

(22) PCT Filed: Jan. 21, 2011

(86) PCT No.: PCT/JP2011/051042
§ 371 (c)(1),
(2), (4) Date: Jul. 27, 2012

(87) PCT Pub. No.: WO2011/093209
PCT Pub. Date: Aug. 4, 2011

(65) Prior Publication Data
US 2012/0300174 A1 Nov. 29, 2012

(30) Foreign Application Priority Data
Jan. 29, 2010 (JP) ................................ 2010-018380

(51) Int. Cl.
*A61B 3/10* (2006.01)
(52) U.S. Cl.
CPC ...................................... *A61B 3/101* (2013.01)
(58) Field of Classification Search
USPC ............................. 351/208, 219, 247; 600/356
See application file for complete search history.

(56) References Cited

U.S. PATENT DOCUMENTS

| 2002/0180929 A1* | 12/2002 | Tseng et al. | 351/206 |
|---|---|---|---|
| 2006/0109423 A1* | 5/2006 | Wang | 351/206 |
| 2009/0168019 A1* | 7/2009 | Tuan | 351/206 |
| 2009/0201465 A1* | 8/2009 | Huth | 351/205 |
| 2012/0057126 A1* | 3/2012 | Chang et al. | 351/206 |

FOREIGN PATENT DOCUMENTS

| JP | 3556033 | 8/1997 |
|---|---|---|
| JP | 3699853 | 9/2000 |
| JP | 2000287930 | 10/2000 |
| JP | 3718104 | 11/2001 |
| JP | 2007209370 | 8/2007 |
| JP | 2009178174 | 8/2009 |

OTHER PUBLICATIONS

Hatta, Yoko et al., "Tear film lipid layer in dry eyes" in: Japanese Journal of Clinical Ophthalmology, vol. 49, No. 5, Igaku-Shoin Ltd., May 15, 1995, pp. 847-851 (English-language Abstract).

* cited by examiner

*Primary Examiner* — Suchin Parihar
*Assistant Examiner* — William R Alexander
(74) *Attorney, Agent, or Firm* — Adams & Wilks

(57) ABSTRACT

A ophthalmologic method and apparatus for processing a captured image of a tear film lipid layer on a cornea of a patient's eye to be examined and for classifying types of dry eye of the patient's eye. The captured image of the tear film lipid layer is processed to measure a movement speed of the tear film lipid layer at the time of opening of the patient's eyelid. The captured image of the tear film lipid layer is further processed to measure a time until the tear film lipid layer is broken up after the patient's eyelid has been opened and a break up region is detected. The type of dry eye of the patient's eye is classified based on the two measurement results.

8 Claims, 8 Drawing Sheets

OPHTHALMOLOGIC APPARATUS AND IMAGE CLASSIFICATION METHOD

CROSS-REFERENCE TO RELATED APPLICATIONS

This application is a U.S. national stage application of International Application No. PCT/JP2011/051042 filed Jan. 21, 2011, claiming a priority date of Jan. 29, 2010, and published in a non-English language.

BACKGROUND OF THE INVENTION

1. Technical Field

The present invention relates to an ophthalmologic apparatus and an image classification method, and more specifically to an ophthalmologic apparatus and an image classification method for quantitatively measuring abnormalities in the quantity and quality of tear film and classifying types of dry eye.

2. Background Art

In recent years, the number of patients with dry eye has increased due to an increase in the number of visual display terminal (VDT) workers, drying of rooms by air-conditioning, and the like. There is a risk that disorders in the corneal epithelium, conjunctival disorders, and various other ophthalmic disorders may occur in conjunction with dry eye, and the diagnosis of dry eye has become an important subject of ophthalmologic diagnosis.

Diagnosis of dry eye has been conventionally performed by vital staining test, a test of the amount of tear fluid secretion by Schirmer's test, and the like. However, there are problems in reproducibility of test results and objectivity because of the involvement of chemical eye drops and contact with foreign objects with the result of unavoidable pain for the examinee.

In order to diagnose dry eye without contact, the change with time of a dry spot region generated from the break up of the tear film after opening the eyelid of the eye to be examined is measured as a change with time in area ratio data of the dry spot region, and the change with time in the dry spot region is displayed on a monitor to check abnormalities in the stability of tear film in dry eyes (Patent Document 1).

Furthermore, in order to quantitatively evaluate abnormality in the tear fluid in the dry eye, diagnosis of dry eye is also performed by measuring the intensity of an interference pattern due to interference of reflected light on the obverse and reverse surfaces of the tear film lipid layer and calculating a value showing an abnormality in the tear film in the dry eye from the measured value (Patent Document 2), or setting a plurality of areas in the image of the interference pattern and evaluating the tear film surface layer on the basis of the hue of each area (Japanese Patent 3), or analyzing the change of the hue of interference fringes with time (Patent Document 4). Diagnosis of abnormality in the tear film in the dry eye is also performed by imaging the tear film lipid layer on the cornea and calculating the movement speed of the tear film lipid layer at the time the eyelid is opened (Patent Document 5).

Additionally, the tear film is observed without staining with fluorescein, and the time until the tear film is broken up and forms a dark-area (DARK-AREA), i.e., non-invasive break up time (NIBUT) is measured to evaluate abnormality in the tear film in the dry eye (Non-Patent Document 1).

PRIOR ART DOCUMENTS

Patent Documents

Patent Document 1: Japanese Patent No. 3699853
Patent Document 2: Japanese Laid-Open Patent Publication No. 2000-287930
Patent Document 3: Japanese Patent No. 3556033
Patent Document 4: Japanese Patent No. 3718104
Patent Document 5: Japanese Laid-Open Patent Publication No. 2007-209370

Non-Patent Documents

Non-Patent Document 1: "Dry Eye Diagnosis PPP, Testing of Corneal Epithelium/Fluorescein Staining, and Testing for Dry Eye Diagnosis" (May 1, 2002, Edited by Dry Eye Research Society; Publisher: Shunji Nakao, Publishing Office: Medical View Co., LTD), pp. 41 to 45

Methods for measuring and evaluating the interference fringe formed by the tear film lipid layer using such conventional apparatuses (Patent Documents 2, 3, 4) provide low brightness contrast in the interference fringe and there is a problem in that reliable quantification of the abnormality in the tear film in a dry eye is difficult. The method for measuring the change with time in the dry spot that is generated from the tear film break up after the eyelid of the eye to be examined is opened as described in Patent Document 1 has also a problem in that it is difficult to determine the dry spot and quantification is also difficult. Classification of the type of dry eye cannot be determined in detail even when the method according to Patent Document 5 or the NIBUT method according to Non-Patent Document 1 is used.

The present invention was devised in order to solve these problems, and an object thereof is to provide an ophthalmologic apparatus and an image classification method having a simple configuration, with which abnormalities in the tear film in a dry eye can be quantitatively measured with good reliability, and with which types of dry eye can be classified.

SUMMARY OF THE INVENTION

The present invention is characterized by an ophthalmologic apparatus having an optical system for projecting an illumination light onto a tear film lipid layer on a cornea of an eye to be examined, and imaging means for receiving reflected light from the tear film lipid layer and capturing an image of the tear film lipid layer, the ophthalmologic apparatus comprising:

first measuring means for processing the captured image of the tear film lipid layer to measure the movement speed of the tear film lipid layer at the time an eyelid is opened;

second measuring means for processing the captured image of the tear film lipid layer to measure the time until the tear film lipid layer is broken up after the eyelid has been opened and a break up region appears; and classification means for classifying the type of dry eye of the eye to be examined from measurement results from the first and second measuring means.

Furthermore, the present invention is characterized by a method for processing a captured image of a tear film lipid layer on a cornea of an eye to be examined and classifying types of dry eye of the eye to be examined, the method comprising:

processing the captured image of the tear film lipid layer to measure the movement speed of the tear film lipid layer at the time of opening the eyelid;

processing the captured image of the tear film lipid layer to measure the time until the tear film lipid layer is broken up after the eyelid has been opened and a break up region appears; and classifying the type of dry eye of the eye to be examined from the two measurement results.

In the present invention, classification of types of dry eye is performed on the basis of the movement speed of the tear film lipid layer at the time of opening the eyelid that is obtained by processing the captured image of the tear film lipid layer, and of the time elapsed until the break up region appears that is generated by the break up of the tear film lipid layer on the cornea of the eye to be examined after opening the eyelid. Therefore, it is easy to determine the type of dry eye, and it is possible to perform diagnosis and treatment according to the abnormality of the tear film of the dry eye.

DETAILED DESCRIPTION OF THE INVENTION

Figure 1:
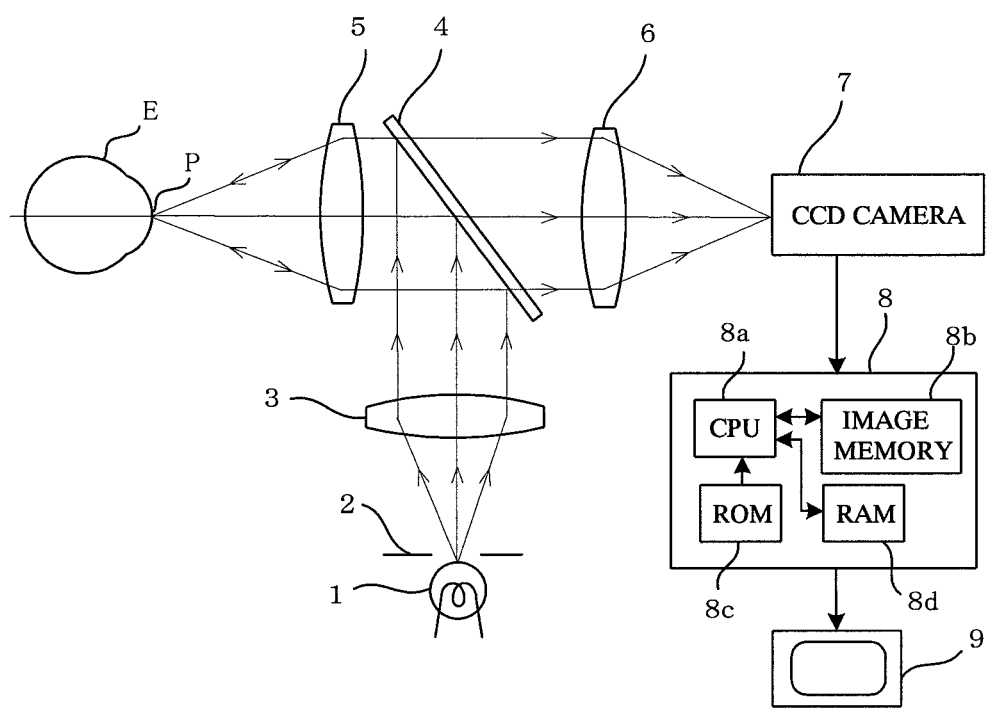
FIG. 1 is an optical view showing a general configuration of the ophthalmologic apparatus according to the present invention.

In the present invention, abnormalities in the tear film in a dry eye are measured using two measuring methods and the type of dry eye is classified based on each of the results. The present invention will be described hereinafter with reference to the embodiments shown in the drawings.

Embodiments

FIG. 1 shows a general configuration of the ophthalmologic apparatus according to the present invention. Reference numeral 1 in the drawing indicates a white light source for illuminating an eye E to be examined, and it is composed of a halogen lamp or the like. Light emitted from the white light source 1 passes through a mask 2 for limiting the illumination field of view, and then illuminates a predetermined point P on the eye E to be examined via a lens 3, a half mirror 4, and a lens 5. The position of point P is selected on the tear film on the cornea of the eye E to be examined. The light intensity of the white light source 1 can be adjusted by an intensity adjusting circuit (not shown).

Reflected light from point P forms a variety of interference patterns depending on the thickness and other states of the lipid layer (lipid film) of the topmost layer of tear film. The reflected light from the tear film lipid layer is received by a color CCD camera (imaging means) 7 via the lens 5, the half mirror 4, and a lens 6. The tear film lipid layer is imaged by the CCD camera 7 as a color image (RGB image), whose image signal (RGB signal) is recorded in an image memory 8b of an image processing device 8. As described later, the image processing device or a CPU 8a thereof constitutes a measuring means (first measuring means) in which the image recorded in the image memory 8b is processed to measure the movement speed of the tear film lipid layer at the time the eyelid is opened. Captured images and processed images are displayed on a monitor 9.

Figure 2:
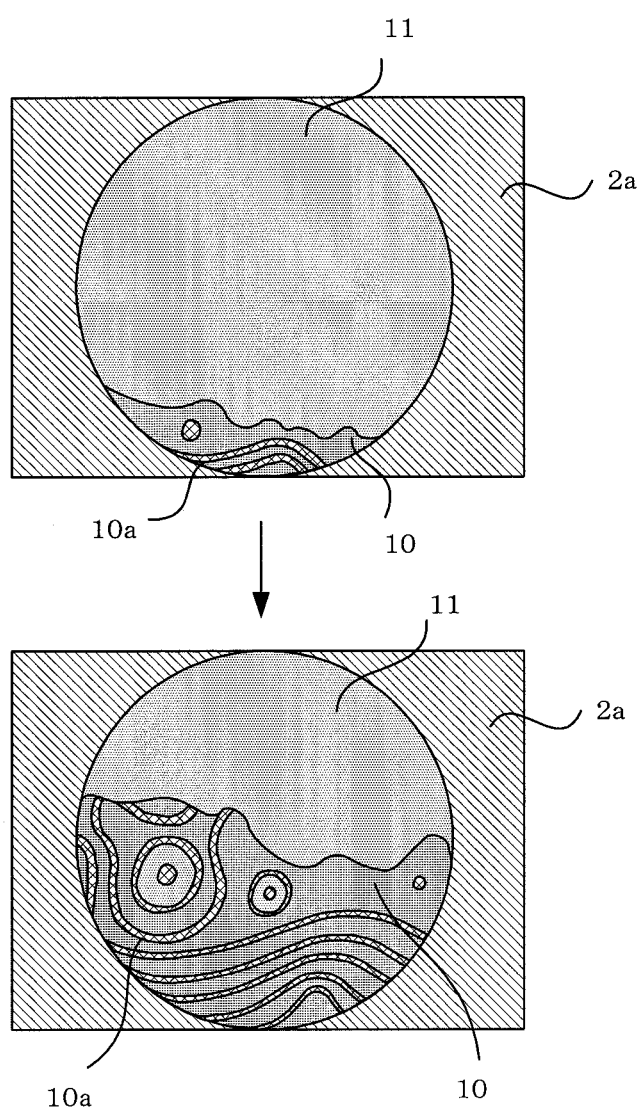
FIG. 2 is an illustrative view showing a spread of the tear film lipid layer.

As shown in FIG. 2, the tear film lipid layer 10 spreads on a cornea 11 as shown from top to bottom after the eyelid is opened. Reference symbol 10a shows a lipid film pattern (interference pattern) from the interference of reflected light on the obverse and reverse surfaces of the tear film lipid layer 10, and 2a shows an image of the mask 2. According to flowchart of FIG. 3, the image processing device 8 analyzes how the tear film lipid layer 10 spreads.

Figure 3:
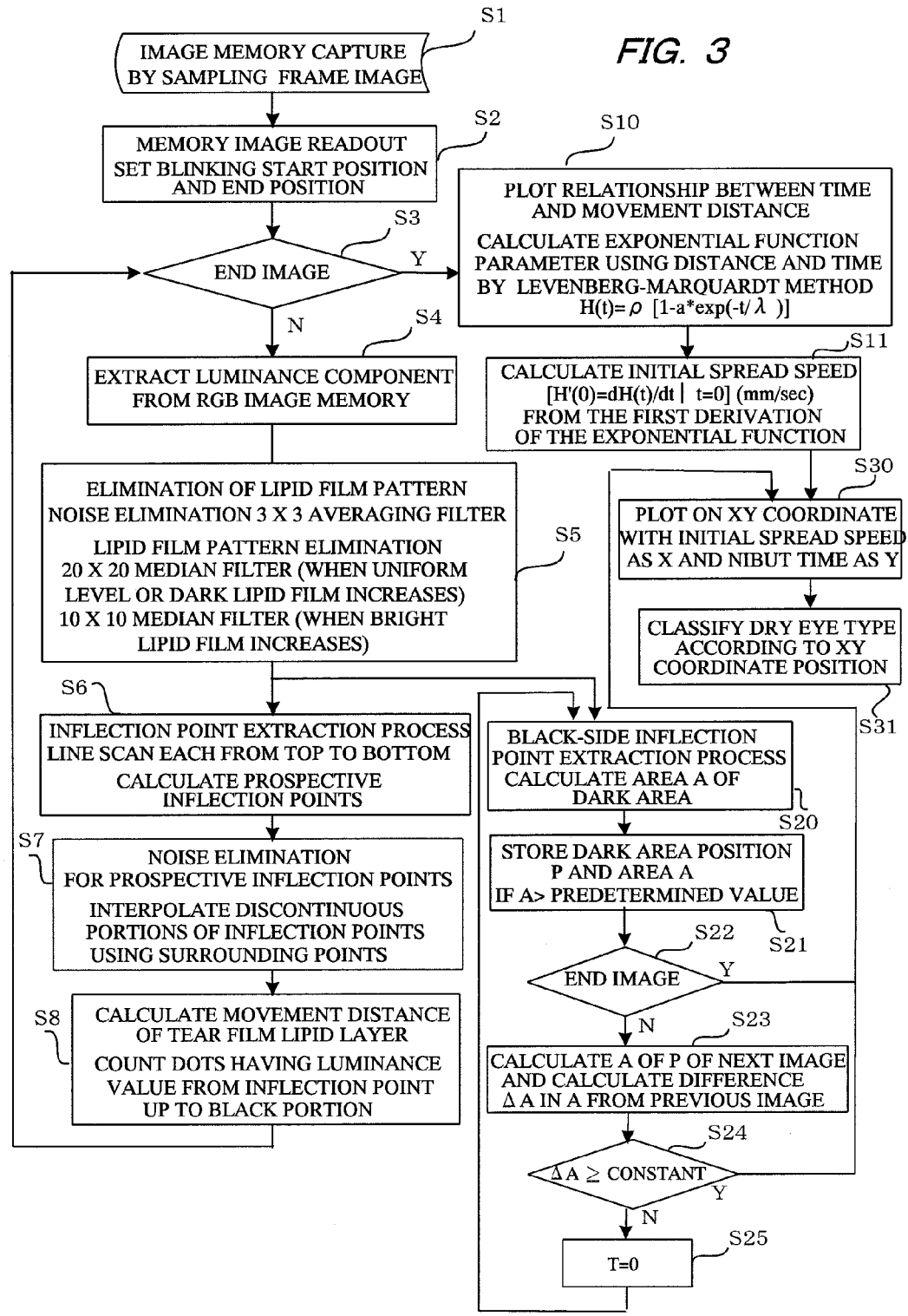
FIG. 3 is a flowchart showing the processing flow by the present invention.

Each procedure shown in the flowchart of FIG. 3 is stored as a program in a ROM 8c (a non-transitory computer readable medium) of the image processing device 8, and the CPU 8a reads out this program and executes each procedure. At this time, a RAM 8d provides working memory and stores various data.

First, a color image of the tear film lipid layer that is imaged with the CCD camera 7 is sampled, for example, every 0.05 seconds, and each sampled image is recorded in sequence in the image memory 8b (Step S1).

The sampled color image of the tear film lipid layer is then read out from the image memory 8b (Step S2). At this time, a blinking start time (blinking start position) and an end time (end position) are set.

The images from the blinking start time, i.e., the time the eyelid is opened, to the end time are read out in sequence from the image memory 8b, and the process proceeds to Step S4 and extracts the luminance component of the read out image as long as the image is not the end point image (N in Step S3).

Figure 4:
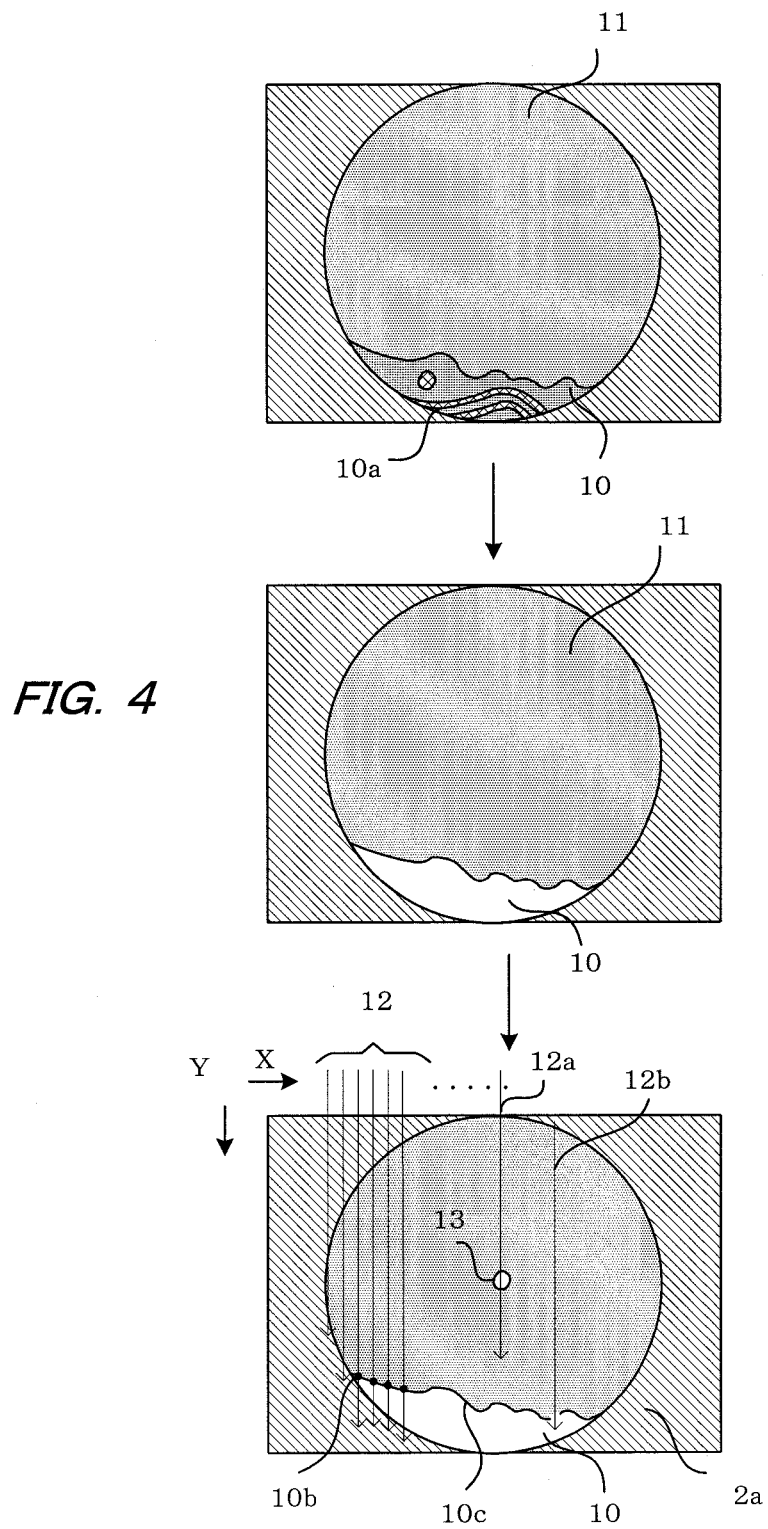
FIG. 4 is an illustrative view showing the flow for calculating the movement distance of the tear film lipid layer on a cornea.

In the following Step S5, noise from the image of the tear film lipid layer 10 is eliminated using a 3×3 averaging filter, and the lipid film pattern 10a is eliminated using a median filter to perform smoothing of the image of the tear film lipid layer. A 20×20 median filter is used as the median filter when the image has uniform level or when a dark lipid film increases, and a 10×10 median filter is used when a bright lipid film increases. The top image of FIG. 4 shows an image in an initial state of the spread of the tear film lipid layer 10, and the middle image of FIG. 4 shows a smoothed image when the lipid film pattern 10a and the noise are eliminated by the process of Step S5.

Next, in Step S6, the contour of the tear film lipid layer 10, i.e., the inflection point where the luminance changes at a portion of the tear film lipid layer is extracted. For this purpose, as shown in the bottom image of FIG. 4, the image is line-scanned by scan lines 12 in the vertical direction (Y) from top to bottom and in the horizontal direction (X) from left to right.

The luminance sum SumPrev (i) of the image of the width m of the vertical direction address n prior in the vertical direction address i is expressed as $$SumPrev(x, y) = \sum_{k=y-n-m/2}^{k=y-n+m/2} Y(k)$$

where x is the target address in the vertical direction, y is the target address in the horizontal direction, n is the up/down direction movement part from the target address, and m is the comparative width.

The luminance sum SumAfter (i) of the image of the width m of the vertical direction address n later in the vertical direction address i is expressed as $$SumAfter(x, y) = \sum_{k=y+n-m/2}^{k=y+n+m/2} Y(k)$$

The luminance of the smoothed image of the tear film lipid layer 10 may be less than or greater than the luminance of the cornea 11 depending on the illumination situation of the eye to be examined. Therefore, the absolute value of the difference between the two is calculated and if the result is greater than a predetermined threshold value, that is, if

|SumPrev(x,y)−SumAfter(x,y)|>Threshold value, then this is set to be an inflection point y(x). This is performed at y=0 to Ywidth (image size in the vertical direction) for each x=0 to Xwidth (image size in the horizontal direction) to sequentially detect inflection points. However, those satisfying the conditions SumPrev (x, y)>Black threshold, and SumAfter (x, y)>Black threshold are selected in order to avoid images of eyebrows, masks 2, and the like.

The inflection points thus detected are shown with reference symbol 10b in the bottom image of FIG. 4. When, for example, noise 13 is detected as an inflection point as in scan line 12a or an inflection point cannot be detected as in scan line 12b during inflection point detection, interpolation is performed with the previous and subsequent inflection points to provide the inflection point (Step S7).

In the present invention, the movement distance (spread distance) of the tear film lipid layer 10 is measured to calculate the movement speed of the tear film lipid layer at the time the eyelid is opened, i.e., the initial spread speed of the tear film lipid layer for quantification of abnormality in the tear film in the dry eye. The movement distance of the tear film lipid layer 10 can be obtained by counting the dots of a portion having a luminance value from the inflection point 10b on one scan line, e.g., a scan line for scanning the center of the cornea image, to the image 2a (black portion) of the mask 2 under and along that scan line. Alternatively, the movement distance of the tear film lipid layer 10 can be made to be the average value of the distance to the mask image 2a from each inflection point obtained from several scan lines before and after a single scan line, or the average value of the distance to the mask image 2a from each inflection point 10b obtained by every scan line 12 for scanning the cornea image. After the movement distance of the tear film lipid layer is obtained, it is stored to the RAM 8d (Step S8).

Figure 6:
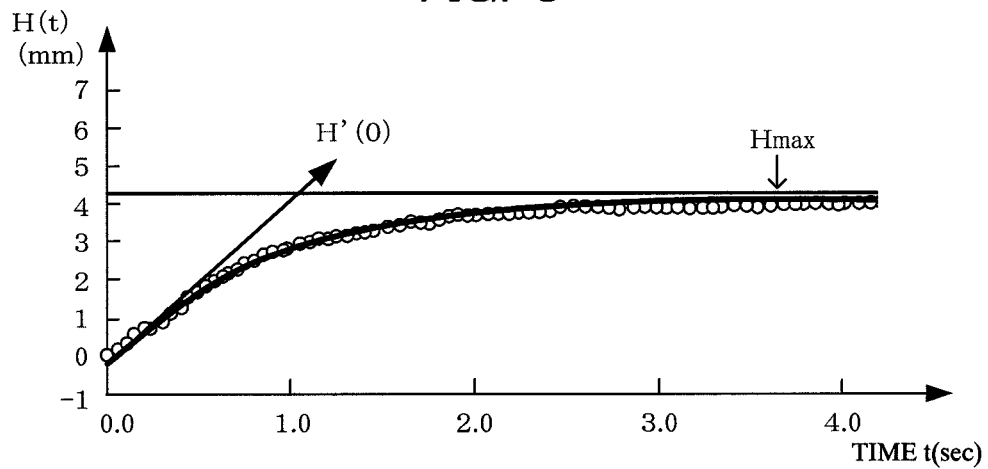
FIG. 6 is a diagram showing the change with time in the movement distance of the tear film lipid layer on a cornea.

When the movement distance shown in Step S8 is obtained for every sampled image, the process proceeds from Step S3 to Step S10, and the relationship between each sampling time (time t) and the movement distance H is plotted. This relationship is shown with round points in FIG. 6. An exponential function H(t)=ρ[1−a*exp(−t/λ)] as shown with the solid line is acquired from this curve by the Levenberg-Marquardt Method. Here, H(t) is the distance (mm), ρ and a are constants, t is the time (sec), and λ is the relaxation time (sec).

The tear film lipid layer 10 spreads in this manner on the cornea after the eyelid has been opened, and the spread behavior can be approximated by an exponential function. The tear film lipid layer can therefore be treated as a viscoelastic body, and the spread behavior thereof can be analyzed using a rheology model, i.e., a Voigt model.

Figure 8:
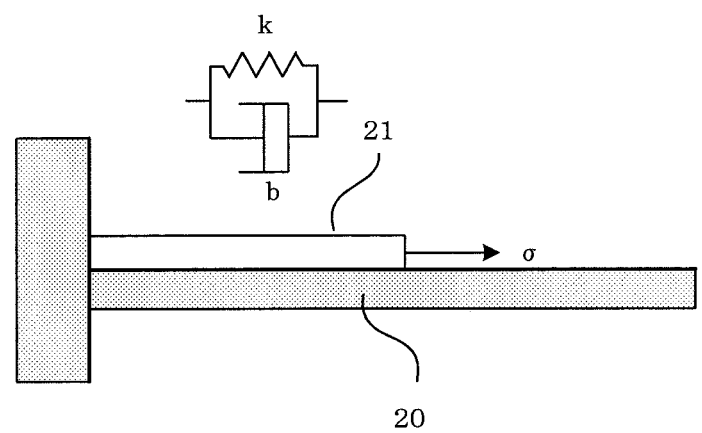
FIG. 8 is an illustrative view showing a state of modeling the tear film lipid layer on a cornea.

FIG. 8 is an illustration of the tear film lipid layer 21 on an eyeball 20 in order to describe the modeling of the tear film lipid layer, and the left edge of the tear film lipid layer 21 is fixed and stress σ (force per unit area) is considered to act on this tear film lipid layer 21. Note that the friction between the eyeball 20 and the tear film lipid layer 21 is considered to be negligible. The spread of the tear film lipid layer 21 at this time can be viewed as the distortion ε relative to the stress σ (spread amount/original length: dimensionless quantity). The relationship of the stress σ and the distortion ε applied to the tear film lipid layer is $$\sigma = k\varepsilon + b\frac{d\varepsilon}{dt}$$

where k is the elastic coefficient (spring coefficient), b is the attenuation coefficient, and t is time.

Figure 7:
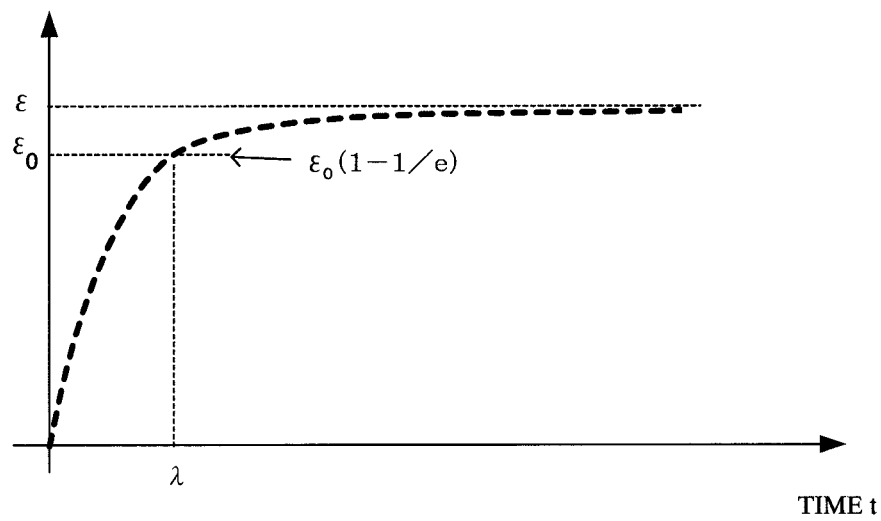
FIG. 7 is a diagram showing the change with time in a modeled tear film lipid layer.

When the above-mentioned equation is integrated, $$\varepsilon = \frac{\sigma_0}{k} + C\exp\left(-\frac{k}{b}t\right)$$

is obtained, where C is a constant. FIG. 7 shows a graph of the relationship in which the distortion ε is set on the vertical axis and the time t is set on the horizontal. The graph represents the distortion ε (change in length) of the tear film lipid layer when the tear film lipid layer is pulled up with a fixed stress. In FIG. 7, reference symbol λ shows the relaxation time.

Here, 16 examples of 22 healthy eyes (all female; average age: 67.4 years old) without meibomian gland dysfunctions yet including dry eyes were selected as eyes to be examined. The change with time in the movement distance H of the tear film lipid layer 10 during spread was calculated for each eye to be examined from images of each tear film lipid layer sampled every 0.05 seconds along the flow shown in FIG. 3. The characteristics shown in FIG. 6 appeared for the entire change with time and it became apparent that the spread of the tear film lipid layer can be analyzed through a Voigt model by assuming that the tear film lipid layer is a viscoelastic body.

In Step S11 of FIG. 3, the change with time of the movement distance of the tear film lipid layer is applied to a Voigt model and analyzed to calculate the initial spread speed of the tear film lipid layer (rate of time change of lipid layer movement distance at the time the eyelid is opened), i.e., the first derivation H'(0)=dH(0)/dt(t=0)(mm/sec) of the exponential function at time t=0 calculated in Step S10.

Japanese Laid-Open Patent Publication No. 1999-267102 describes a method in which the image magnification of the aperture projected onto the tear fluid surface is obtained and from this image magnification the radius of curvature R of the tear fluid surface (tear meniscus) along the margin of the lower eyelid is computed to evaluate the severity of the dry eye from the radius of curvature R. It has been made apparent that this radius of curvature R is used as a value for indicating the amount of tear fluid retained on the ocular surface with good reliability.

The tear meniscus radius of curvature R (mm) was measured for each eye to be examined described above and the relationship between this and the initial spread speed H'(0) of the tear film calculated in Step S11 was checked. This clarifies a significant positive linear correlation between H'(0) and R.

From this technique, it is apparent that the tear film lipid layer spreads in all eyes to be examined while exhibiting behavior similar to a viscoelastic body after the eyelid has been opened, and the initial spread speed thereof increases in proportion to the increase in the amount of retained tear fluid.

In this manner in the present invention, the spread behavior (change with time of the lipid layer movement distance) is analyzed using a rheology model to measure a rate of time change of the movement distance of the tear film lipid layer at the time the eyelid is opened (t=0), i.e., the movement speed (lipid layer initial spread speed) of the tear film lipid layer at the time the eyelid is opened.

Also in the present invention, the appearance time of a break up area (dark area) is measured with a Non-Invasive Break Up Time (NIBUT) method without staining with fluorescein to evaluate the reduction in stability of the tear film in a dry eye.

In this measurement, the examinee is made to blink several times, and is instructed to open the eyelid naturally and not blink when the tear film is judged to have stabilized. In this state, the anterior ocular segment is video-recorded (or still image-captured in succession in short time intervals) to measure the time change of the obtained images, and the time when the dark area appears is measured. In this case, the image processing device 8 or the CPU 8a thereof becomes the measuring means (second measuring means) for measuring the time until the dark area that is generated from the break up of the tear film lipid layer appears.

This measurement of the time of appearance of the dark area is performed simultaneously with the measurement of the movement speed of the tear film lipid layer via the loop processing of Steps S20 to S25, which are branched and performed from Step S5 in FIG. 3. However, in order to perform the measurement of the dark area appearance time under ideal conditions, it can be performed separately from the measurement of the movement speed of the tear film lipid layer.

In Step S20, the image is line-scanned by the scan lines 12 from top to bottom in the vertical direction (Y) and from left to right in the horizontal direction (X) in parallel with the processing of Step S6 to extract black-side inflection points. As shown in the top image of FIG. 5, the luminance value in the region 14 decreases rapidly (decreases as much as or more than a predetermined value) and then increases to restoration. The dots in the region where the luminance value decreases are counted to calculate the area A of the region 14.

The area A may be dark area when it exceeds a predetermined value. Therefore, the area A and its position P are saved to the RAM 8d (Step S21). The position P can be the center position of the region 14.

Next, as long as the image is not the end image (N for Step S22), the area A of the region at position P in the next image is calculated, and the difference ΔA from the area of the region 14 of the previous image that was saved is calculated (Step S23). Then, it is judged whether the ΔA is a value meeting or exceeding a positive constant value (Step S24).

Figure 5:
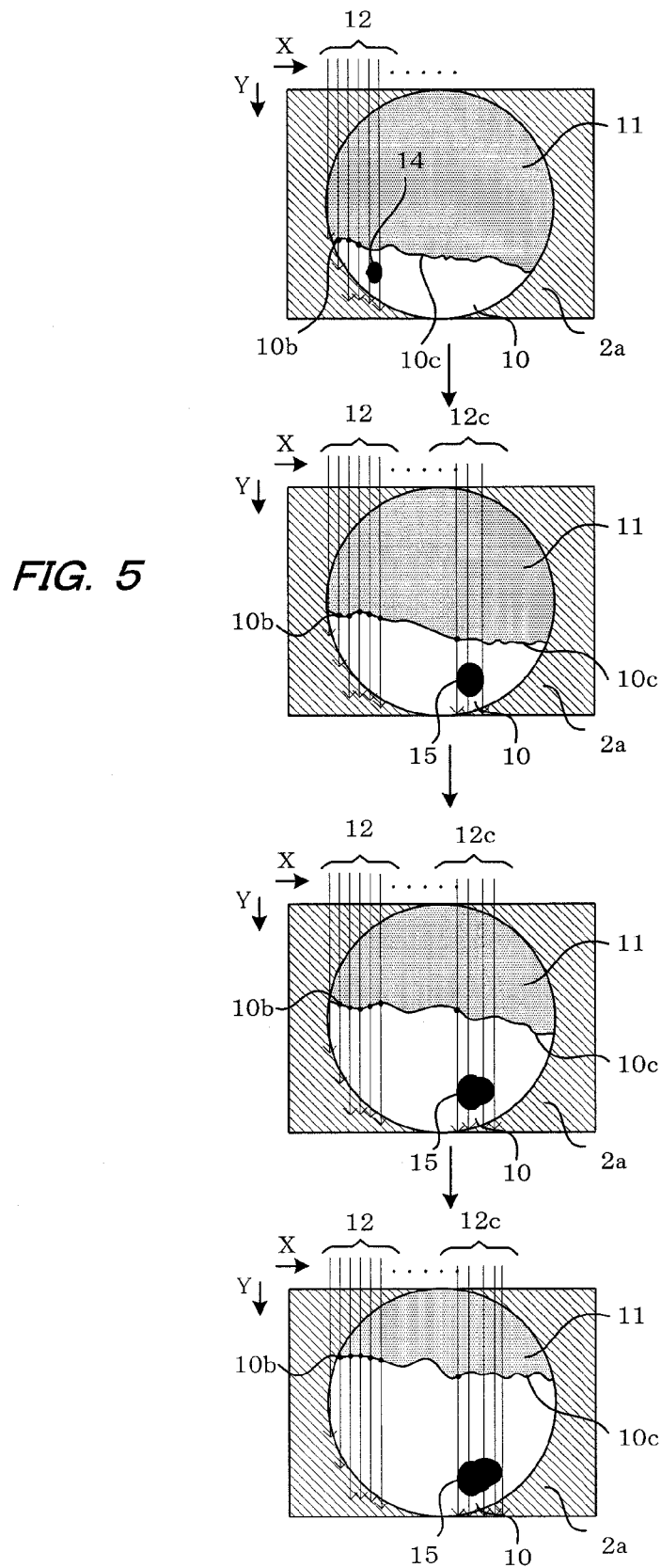
FIG. 5 is an illustrative view showing the flow for calculating the surface area of a dark area on a cornea.

The portion of the region 14 disappears in the next image in the example shown in FIG. 5, so that the ΔA is a negative value. The condition for Step S24 is not met, and the region 14 is not judged as being a dark area. The appearance time T of the dark area is therefore initialized (Step S25), the process returns to Step S20, and the same black-side inflection point extraction processing is performed.

In the second image from the top in FIG. 5, the region 15 is judged by the scan line 12c as an image having the possibility of a dark area. Therefore, its position P and area A are saved and the difference in area ΔA from the region 15 of the previous image is calculated (Step S23). The third image from the top in FIG. 5 shows the next image and the bottom image in FIG. 5 shows the next image thereafter. The region 15 is increasing as the time passes, and the conditions of Step S24 are met, so that the region 15 is judged as being a dark area, and the appearance time T thereof is saved to the RAM 8d.

The dark area appears in only one location in the example in FIG. 5. However, when a plurality of dark areas appear, the judgment of Step S24 can be performed for each of the positions P and the time that satisfies the judgment first can be saved as the dark area appearance T.

Although the judgment of Step S24 is described as being the difference in area ΔA from the previous image, the image difference from a predetermined number of previous images (e.g., multiple images such as two or three images) can be used as ΔA.

When the appearance time T of the dark area is measured in this manner (Y in Step S24) or when the images end without detection of a dark area (Y in Step S22), the process proceeds to Step S30 and the initial spread speed H'(0) of the tear film lipid layer that is calculated in Step S11 is plotted on the horizontal axis (X) and the appearance time T of the dark area (NIBUT) is plotted on the vertical axis (Y).

In the present embodiment, a two-dimensional map is created in accordance with the initial spread speed H' of the tear film lipid layer and the appearance time T of the dark area that are plotted respectively on X, Y of an XY coordinate, and the type of dry eye is classified (Step S31).

Figure 9:
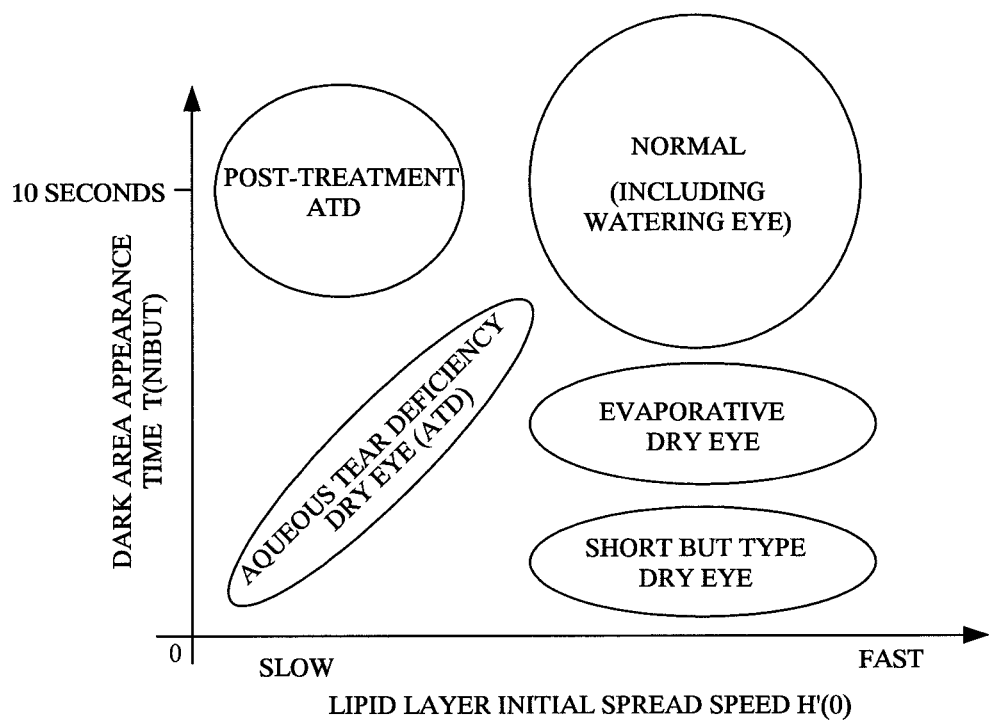
FIG. 9 is an illustrative view showing the classification of the types of dry eye.

In FIG. 9, the types of dry eye are classified according to the initial spread speed H'(0) of the tear film lipid layer and the appearance time T of the dark area by the NIBUT method into the following five types: "Aqueous Tear Deficiency (ATD) dry eye", "short Break Up Time (BUT) type dry eye", "evaporative dry eye", "post-treatment ATD", and "normal (including watering eye)".

An "ATD dry eye" is a type of dry eye in which the tear fluid amount decreases with an approximately proportionate relationship between the lipid layer initial spread speed and the appearance time T of the dark area, and is characterized in that the appearance time becomes longer as the lipid layer initial spread speed becomes faster. This is a type indicated by a narrow elliptical region that extends to the top right.

A "short BUT type dry eye" is a type of dry eye in which the time until the tear film is broken up and generates a dark area is short, and is positioned to the bottom right because the lipid layer initial spread speed is high and the appearance time is short. This is a type indicated by a substantially circular region.

An "evaporative dry eye" is a type of dry eye in which the evaporation of the tear fluid is accelerated and the lipid layer initial spread speed is the same as in the short BUT type dry eye, and is a type with a longer appearance time of the dark area than in the short BUT type dry eye. Types that are caused by a meibomian gland dysfunction have a thin lipid layer, so that the tear film lipid layer is observed in a high-magnification mode for its identification. Furthermore, this includes the case in which plugs are inserted in severe ATD as a special example.

A "post-treatment ATD" is an ATD dry eye that is classified when the eye has been treated with, for example, eye drops for causing mucin to be secreted or for increasing the tear fluid amount. Post-treatment ATD is characterized in that the appearance time of the dark area becomes longer while the lipid layer initial spread speed is slow, and is a type that is positioned to the top left of the ATD dry eye and indicated by a substantially circular region. The fact that the appearance time of the dark area is long (the tear film is stable) even though the lipid layer initial spread speed is slow (the tear film on the cornea is thin, i.e., the water content of the tear fluid on the cornea is low) shows that there was an effect by the treatment, and provides useful information for the development of new medicines.

"Normal" is an eye without dry eye including watering eye.

The regions shown in circles or ellipses in FIG. 9 do not show the limits of each type of dry eye, but qualitatively and schematically show the regions that indicate their characteristics, and the blank regions between each region can be classified into the type of the closest region, for example, according to the measurement results.

The lipid layer initial spread speed is an indicator for showing the amount of tear fluid because the lipid layer initial spread speed correlates with the thickness of the tear fluid on the cornea (when the tear film on the cornea is thin, the lipid layer spread becomes poor and the initial speed thereof becomes slow). On the other hand, the appearance time of the dark area (NIBUT) is an indicator for showing the quality of the tear fluid, i.e., the stability of the tear film because the appearance time of the dark area shows that the tear fluid is quickly broken up and has poor stability when the time thereof is short and that the tear film is stable when the time thereof is long.

In the present embodiment, an indicator for showing the amount of tear fluid is applied to one axis (X-axis), and an indicator for showing the quality of the tear fluid is applied to the other axis (Y-axis) to classify the types of dry eye. Therefore, determination of the type of dry eye is made simple, and diagnosis and treatment are made possible in accordance with the type of dry eye, as shown in FIG. 9.

In the embodiment described above, the movement distance of the tear film lipid layer was calculated and the movement speed (initial spread speed) of the tear film lipid layer was measured, but it is also possible to measure the change with time of the area of the tear film lipid layer to calculate the initial spread speed.

The area of the tear film lipid layer is calculated after steps S6, S7 in FIG. 3 as an area under the inflection point line $10c$, shown in the bottom image of FIG. 4, that connects the detected inflection points together, i.e., by counting the number of dots (number of pixels) of the portion having a luminance value up to the image $2a$ (black portion) of the mask 2 in the area below an inflection point line $10c$. When the areas are calculated for every image that has been sampled, an exponential function similar to the one shown in FIG. 6 can be obtained by plotting the relationship between each sampling time (time t) and area S, and the rate of time change of the lipid layer area at the time the eyelid has been opened, i.e., the first derivation $S'(0)=dS(t)/dt\ (t=0)(mm^2/sec)$ of the exponential function obtained at the time $t=0$ can be calculated and used as the initial spread speed of the tear film lipid layer.

In this manner, the severity of dry eye can be quantified by measuring the (1) lipid layer initial spread speed (method of viewing by movement distance H), (2) lipid layer initial spread speed (method of viewing by area S), and (3) appearance time of the dark area (NIBUT).

Furthermore, the severity of dry eye can also be quantified by measuring (4) the range of the tear film lipid layer (movement distance Hmax in FIG. 6), and as described in Japanese Laid-Open Patent Publication No. 1999-267102, it is possible to calculate (5) the radius of curvature R of the tear fluid surface (tear meniscus) along the lower eyelid margin, and the severity of dry eye is quantified from the radius of curvature R.

In FIG. 9, the types of dry eye were classified using the parameters of (1) and (3), but the types of dry eye can be classified by combining two or three of any of (1) to (5).

KEY TO SYMBOLS 2 mask
7 CCD camera
8 image processing device
10 tear film lipid layer
11 cornea
15 dark area

The invention claimed is:

1. An ophthalmologic apparatus comprising:
   an optical system for projecting an illumination light onto a tear film lipid layer on a cornea of a patient's eye to be examined;
   imaging means for receiving reflected light from the tear film lipid layer onto which the illumination light is projected and for capturing an image of the tear film lipid layer;
   first measuring means for processing the captured image of the tear film lipid layer to measure a movement speed of the tear film lipid layer at the time an eyelid of the patient is opened;
   second measuring means for processing the captured image of the tear film lipid layer to measure a time until the tear film lipid layer is broken up after the patient's eyelid has been opened and a breakup region appears; and
   classification means for classifying the type of dry eye of the patient's eye based on measurement results from the first and second measuring means and displaying the type of dry eye as a two-dimensional map having one coordinate axis representing the movement speed of the tear film lipid layer at the time the patient's eyelid is opened and the other coordinate axis representing the time until the tear film lipid layer is broken up after the patient's eyelid has been opened and the breakup region appears.

2. An ophthalmologic apparatus according to claim 1; wherein the second measuring means determines that the breakup region has been detected when a region having a significantly different luminance is detected in the same position in succession from a plurality of captured images.

3. An ophthalmologic apparatus according to claim 1; wherein the classification means classifies the type of dry eye into at least five types of dry eye based on the measurement results of the first and second measurement means.

4. An ophthalmologic apparatus according to claim 2; wherein the classification means classifies the type of dry eye into at least five types of dry eye based on the measurement results of the first and second measurement means.

5. A non-transitory computer readable medium including a computer program having instructions that cause a computer to:
   process an image of a tear film lipid layer on a cornea of the patient's eye to measure an initial spread speed of the tear film lipid layer at a time when an eyelid of the patient is opened, and to measure a time from the opening of the eyelid until a dark area generated from a breakup of the tear film lipid layer appears;

classify and determine the type of dry eye of the patient's eye on the basis of the measurements of the initial spread speed of the tear film lipid layer and the time until the dark area appears; and display the type of dry eye as a two-dimensional map having one coordinate axis representing the spread speed of the tear film lipid layer at the time the patient's eyelid is opened and the other coordinate axis representing the time until the tear film lipid layer is broken up after the patient's eyelid has been opened and the breakup region appears.

6. A non-transitory computer readable medium according to claim 5; wherein the instruction to classify and determine the type of dry eye comprises an instruction to classify the type of dry eye into at least five types of dry eye on the basis of the measurements of the initial movement speed of the tear film lipid layer and the time until the dark area appears.

7. A non-transitory computer readable medium according to claim 5; further comprising an instruction to project illumination light onto the tear film lipid layer and capture the image of the tear film lipid layer onto which the illumination light is projected.

8. A non-transitory computer readable medium according to claim 7; wherein the instruction to classify and determine the type of dry eye comprises an instruction to classify the type of dry eye into at least five types of dry eye on the basis of the measurements of the initial movement speed of the tear film lipid layer and the time until the dark area appears.

* * * * *